(12) United States Patent
Janssen et al.

(10) Patent No.: US 7,247,764 B2
(45) Date of Patent: Jul. 24, 2007

(54) CONVERSION PROCESS

(75) Inventors: Marcel J. G. Janssen, Kessel Lo (BE); Teng Xu, Houston, TX (US); Cor F. Van Egmond, Pasadena, TX (US); Keith H. Kuechler, Friendswood, TX (US); Stephen N. Vaughn, Kingwood, TX (US); James Harding Beech, Jr., Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 376 days.

(21) Appl. No.: 10/462,256

(22) Filed: Jun. 16, 2003

(65) Prior Publication Data

US 2004/0034265 A1    Feb. 19, 2004

Related U.S. Application Data

(63) Continuation-in-part of application No. 10/218,728, filed on Aug. 14, 2002.

(51) Int. Cl.
*C07C 1/00* (2006.01)
*C07C 1/20* (2006.01)

(52) U.S. Cl. .................. 585/640; 585/638; 585/639

(58) Field of Classification Search ............. 585/638, 585/639, 640
See application file for complete search history.

(56) References Cited

U.S. PATENT DOCUMENTS

| | | | |
|---|---|---|---|
| 3,945,944 A | 3/1976 | Kang | |
| 4,062,905 A | 12/1977 | Chang et al. | |
| 4,079,095 A | 3/1978 | Givens et al. | |
| 4,310,440 A | 1/1982 | Wilson et al. | |
| 4,434,314 A | 2/1984 | Hoelderich et al. | 585/640 |
| 4,440,871 A | 4/1984 | Lok et al. | |
| 4,499,327 A | 2/1985 | Kaiser | |
| 4,503,281 A | 3/1985 | Hoelderich et al. | 585/640 |
| 4,673,559 A | 6/1987 | Derouane et al. | |
| 4,677,242 A | 6/1987 | Kaiser | |
| 4,677,243 A | 6/1987 | Kaiser | |
| 4,857,667 A | 8/1989 | Harandi et al. | 585/403 |
| 4,873,390 A | 10/1989 | Lewis et al. | |
| 5,041,690 A | 8/1991 | Harandi et al. | 568/695 |
| 5,047,141 A | 9/1991 | Chu | |
| 5,095,163 A | 3/1992 | Barger | |
| 5,141,729 A | 8/1992 | Chang et al. | |
| 5,166,455 A | 11/1992 | Chin et al. | 568/697 |
| 5,167,937 A | 12/1992 | Harandi et al. | 422/190 |
| 5,313,006 A | 5/1994 | Knifton | 568/698 |
| 5,367,100 A | 11/1994 | Gongwei et al. | |
| 5,491,273 A | 2/1996 | Santiesteban et al. | 585/639 |
| 5,714,662 A | 2/1998 | Vora et al. | 585/640 |
| 5,741,751 A | 4/1998 | Miller | 502/208 |
| 5,942,104 A | 8/1999 | Miller | 208/28 |
| 6,166,282 A | 12/2000 | Miller | |
| 6,740,791 B2 | 5/2004 | Kuechler et al. | |
| 2002/0087041 A1 | 7/2002 | Kuechler et al. | 585/638 |

OTHER PUBLICATIONS

"Alkylation of toluene with methanol on zeolites. The role of electronegativity on the chain or ring alkylation," Girodano, et al., Zeolites, vol. 7, 131-134, 1987, no month.

"Positions of Cations and Molecules in Zeolites with the Chabazite Framework, III. Dehydrated NA-Exchanged Chabazite," Mortier et al., Mat. Res. Bull., vol. 12, pp. 241-249, 1977, no month.

"The synthesis and characterization of SAPO-43," Akporiaye et al., Zeolites, vol. 17, pp. 517-522, 1996, no month.

*Primary Examiner*—Elizabeth D. Wood

(57) ABSTRACT

The invention relates to a conversion process for making olefin(s) using a molecular sieve catalyst composition. More specifically, the invention is directed to a process for converting a feedstock comprising an oxygenate in the presence of a molecular sieve catalyst composition, wherein the feedstock is free of or substantially free of metal salts.

38 Claims, No Drawings

CONVERSION PROCESS

This application is a continuation-in-part of application Ser. No. 10/218,728, filed Aug. 14, 2002.

FIELD OF THE INVENTION

The present invention relates to a conversion process for making olefin(s) using a molecular sieve catalyst composition in the presence of a hydrocarbon feedstock.

BACKGROUND OF THE INVENTION

Olefins are traditionally produced from petroleum feedstock by catalytic or steam cracking processes. These cracking processes, especially steam cracking, produce light olefin(s) such as ethylene and/or propylene form a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion, partial oxidation or reforming reaction of natural gas, mostly methane, and an oxygen source into hydrogen, carbon monoxide and/or carbon dioxide. Syngas production processes are well known, and include conventional steam/methane reforming, autothermal reforming, partial oxidation or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred methanol conversion process is generally referred to as a methanol-to-olefin(s) process, where methanol is converted to primarily ethylene and/or propylene in the presence of a molecular sieve.

Methanol conversion processes into one or more olefin(s) typically takes place in the presence of a molecular sieve. Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Molecular sieves in general have a one-, two- or three-dimensional crystalline pore structure having uniformly sized pores of molecular dimensions that selectively adsorb molecules that can enter the pores, and exclude those molecules that are too large.

There are many different types of molecular sieves well known to convert a feedstock, especially an oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; U.S. Pat. No. 4,310,440 describes producing light olefin(s) from an alcohol using a crystalline aluminophosphates, often represented by $ALPO_4$; and one of the most useful molecular sieves for converting methanol to olefin(s) is a silicoaluminophosphate molecular sieves. Silicoaluminophosphate (SAPO) molecular sieves contain a three-dimensional microporous crystalline framework structure of $[SiO_2]$, $[AlO_2]$ and $[PO_2]$ corner sharing tetrahedral units and is useful in converting a hydrocarbon feedstock into olefin(s), particularly where the feedstock is methanol. See for example, U.S. Pat. Nos. 4,440,871, 4,499,327, 4,677,242, 4,677,243, 4,873,390, 5,095,163, 5,714,662 and 6,166,282, all of which are herein fully incorporated by reference.

These molecular sieves are sensitive to various contaminants resulting in the lowering of their selectivity to produce light olefin(s) and reducing the operability of a conversion process. These contaminants are introduced to a particular conversion process in a variety of ways. Sometimes the molecular sieve itself results in the generation of contaminants affecting the conversion performance of the molecular sieve. In addition, in large scale processes it is more likely that the effect of various contaminants entering into commercial conversion processes are higher.

Therefore, it would be highly desirable to control contamination so as not to adversely affect the molecular sieve catalyst. Controlling contamination is particularly desirable in oxygenate to olefin reactions, particularly in methanol to olefin reactions, where grade A and AA feedstocks, which are typically used, are relatively expensive. Such feedstocks also have to be shipped over large distances, often over large bodies of water, and are highly susceptible to being contaminated during shipping.

SUMMARY OF THE INVENTION

This invention provides for a process for converting a feedstock in the presence of a molecular sieve into one or more olefin(s), while controlling contamination of the feedstock. Contamination of the feedstock can be controlled by providing a feedstock having an appropriate conductivity level. The conductivity level can accurately reflect contamination levels, particularly metals contamination levels, more particularly metal salt contamination, which can have an especially negative impact on molecular sieve catalysts.

In one embodiment, the invention is directed to a process for converting greater than 1000 Kg per hour of a feedstock in the presence of a molecular sieve into one or more olefin(s), wherein the feedstock having a conductivity of not greater than about 10 uS/cm, preferably not greater than about 5 uS/cm, more preferably not greater than about 3 uS/cm, and most preferably not greater than about 2 uS/cm. In another embodiment, the feedstock comprises seawater. In yet another embodiment, the feedstock comprises not greater than about 50 ppm, preferably not greater than about 30 ppm, more preferably not greater than about 20 ppm, and most preferably not greater than about 10 ppm of a Group IA metal salt or a Group IIA metal salt. Preferably the feedstock comprises an oxygenate such as an alcohol and/or an ether, for example methanol and/or dimethyl ether.

In an embodiment, the invention is directed to a process for converting a feedstock in the presence of a molecular sieve in a reactor, the process comprising the steps of: (a) introducing to the reactor a feedstock at a rate of 1,000 Kg of feedstock per hour, preferably greater than 10,000 Kg per hour, wherein the feedstock has a conductivity of not greater than about 10 uS/cm; (b) introducing a molecular sieve to the reactor; and (c) withdrawing an effluent stream from the reactor, the effluent stream comprising greater than 1,000 Kg of one or more olefin(s) per hour. Preferably, the feedstock further comprises an oxygenate such as methanol and/or dimethyl ether and the olefin(s) are ethylene and/or propylene. In a preferred embodiment, the feedstock comprises methanol and a Group IA metal salt, in particular sodium or potassium chloride, and the molecular sieve is a silicoaluminophosphate or aluminophosphate, or a mixture thereof.

In another embodiment, the invention is directed to a process for converting a feedstock in the presence of a molecular sieve or catalyst composition thereof in a reactor to produce greater than 1,000 Kg per hour of one or more olefin(s), the process operating with a feedstock having a conductivity less than 2 uS/cm. Preferably greater than 2,000 Kg per hour of ethylene and/or propylene, and more preferably greater than 4,000 Kg per hour of ethylene and propylene. In this embodiment, the rate of feedstock entering the reactor per day is greater than 100,000 Kg per day.

In yet another embodiment, the invention relates to a process for converting a feedstock, preferably a feedstock comprising an oxygenate, the process comprising the steps of (a) providing a feedstock having a relatively high conductivity such as for example greater than 10 uS/cm; (b) reducing the conductivity of the feedstock to not greater than about 10 uS/cm; preferably not greater than about 5 uS/cm; still preferably not greater than about 3 uS/cm, more preferably not greater than about 2 uS/cm to form a treated feedstock; (c) introducing the treated feedstock into a reactor; (d) providing a molecular sieve catalyst composition in the reactor to convert the treated feedstock into one or more olefin(s); and (e) withdrawing an effluent stream comprising the one or more olefin(s) from the reactor. In a preferred embodiment, the feedstock comprises methanol and seawater.

In another embodiment of all the embodiments described above, the molecular sieve is synthesized from a combination of at least two, preferably at least three, of the group consisting of a silicon source, a phosphorous source and an aluminum source, optionally in the presence of a templating agent. In the most preferred embodiment, the molecular sieve is a silicoaluminophosphate or aluminophosphate, most preferably a silicoaluminophosphate.

In yet another embodiment, there is provided a process for converting oxygenate to olefin, which comprises providing an oxygenate composition having a positive conductivity of not greater than 10 uS/cm and containing at least one Group 1A or Group IIA metal salt. The oxygenate composition is contacted with a molecular sieve to convert oxygenate in the oxygenate composition to olefin. Preferably, the conductivity of the provided oxygenate composition is at least 1.5 uS/cm.

In another embodiment, the process for converting oxygenate to olefin comprises providing an oxygenate composition containing at least one Group 1A or Group IIA metal salt. Preferably, the provided oxygenate composition has a conductivity of not greater than 750 uS/cm, more preferably, a conductivity of not greater than 500 uS/cm, and most preferably a conductivity of not greater than 300 uS/cm. The conductivity of the oxygenate composition is reduced to not greater than 10 uS/cm to form a treated feedstock, and the treated feedstock is contacted with a molecular sieve to convert oxygenate in the oxygenate composition to olefin.

DETAILED DESCRIPTION OF THE INVENTION

I. Introduction

The invention is directed toward a conversion process of a hydrocarbon feedstock, particularly methanol, in the presence of molecular sieve catalyst composition to one or more olefin(s). In this invention, the feedstock is low in contaminants so as not to significantly have an adverse effect on catalyst life or selectivity to desired product. Although the presence of only trace amounts of various contaminants in the feedstock can severely impact the life or selectivity of the molecular sieve catalyst, this invention allows the presence of certain contaminants in the feedstock at low levels. In fact, according to certain preferred embodiments of this invention, the presence of certain metal salts, particularly sodium metal salts, especially sodium chloride, at low concentrations in the feed can actually have a positive effect on selectivity to desired olefin product such as ethylene and propylene.

In one embodiment of the invention, desired or tolerable levels of contaminants in the hydrocarbon feedstock of this invention are determined by the conductivity of the feedstock. The feedstock preferably exhibits a positive conductivity to a level that does not significantly reduce selectivity to desired olefin product. In particular, the positive conductivity of the feedstock is at a level in which the selectivity to ethylene and propylene product is not significantly reduced compared to that of a feedstock having a substantially neutral conductivity. In making conductivity determinations, it is preferable in this invention to use a Schott Geräte Conductivity Measurement Cell (Type CG857; Cell LF100) in the temperature range of from about 7° C. to about 50° C.

In this invention, it is desired that the feedstock have a positive conductivity of not greater than about 10 uS/cm. Preferably, the feedstock has a positive conductivity of not greater than about 5 uS/cm, more preferably not greater than about 3 uS/cm, and most preferably not greater than about 2 uS/cm. According to this invention, positive conductivity means greater than 0 uS/cm. Preferably, the feedstock has a positive conductivity of at least about 1.5 uS/cm.

In another embodiment of the invention, the feedstock contains seawater or metals contained in the feedstock as a result of the feedstock having contacted seawater. The presence of such metals does not have to be directly determined, however. It is sufficient to determine the conductivity of the feedstock to assess the level of contamination. The amount of contaminants present in the feedstock is directly correlatable in this invention to the desired conductivity limits.

In yet another embodiment of the invention, the feedstock contains at least one Group IA or IIA metal salt. Preferred Group IA metal salts include lithium, sodium, and potassium salts. Halide salts of Group IA metals, particularly lithium, sodium, and potassium, are particularly preferred. Particularly desired are chloride salts of lithium, sodium, and potassium. Preferred Group IIA metal salts include magnesium and calcium salts. Halide salts of Group IIA metals, particularly magnesium and calcium, are particularly preferred. The limited presence of sodium chloride is most preferred. Such salts can actually contribute to enhancing, or at least not affecting, selectivity to ethylene and propylene product.

According to this invention, some reduction in catalyst life is acceptable as a result of feedstock containing contaminants, particularly seawater contaminants, more particularly the Group IA and/or Group IIA metal contaminants. Generally, it is preferred that catalyst life be reduced by an amount of not greater than 20% relative to that of a feedstock having a substantially neutral conductivity. Preferably, catalyst life is reduced by an amount of not greater, than 15%, more preferably not greater than 10% relative to that of a feedstock having a substantially neutral conductivity.

In embodiments of the invention in which the feedstock contains seawater, the seawater should be at concentrations in which the conductivity remains within desirable ranges. In one embodiment, the seawater concentration of the feedstock is not greater than 250 wppm, based on total weight of the feedstock. Preferably, the seawater concentration is not greater than 200 wppm, more preferably not greater than 150 wppm, and most preferably not greater than 100 wppm, based on total weight of the feedstock.

II. Molecular Sieves and Catalysts Thereof

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEI, AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, prefer- ably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves are described in R. Szostak, *Handbook of Molecular Sieves,* Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

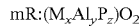

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.0 1. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1.

III. Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment, the molecular sieves are synthesized by forming a reaction product of a source of silicon, a source of aluminum, a source of phosphorous, an organic templating agent, preferably a nitrogen containing organic templating agent. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E. I. du Pont de Nemours, Wilmington, Delaware, silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as ALPO$_4$, phosphorous salts, or combinations thereof. The preferred source of phosphorous is phosphoric acid, particularly when producing a silicoaluminophosphate.

Templating agents are generally compounds that contain elements of Group VB of the Periodic Table of Elements, particularly nitrogen, phosphorus, arsenic and antimony, more preferably nitrogen or phosphorous, and most preferably nitrogen. Typical templating agents of Group VB of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula R$_4$N$^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N', N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source.

A synthesis mixture containing at a minimum a silicon-, aluminum-, and/or phosphorous-composition, and a templating agent, should have a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline product is typically from immediately up to several weeks, the duration of which is usually dependent on the temperature; the higher the temperature the shorter the duration. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

IV. Methods for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into molecular sieve catalyst compositions by combining the synthesized molecular sieve(s) with a binder and optionally, but preferably, a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL200DW available from Nyacol Nano Technologies, Inc., Ashland, Mass.

The molecular sieve described above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a $D_{90}$ particle size distribution of less than about 1 µm.

Upon combining the molecular sieve, the binder, and optionally the matrix material, in a liquid to form a slurry, mixing, preferably rigorous mixing is needed to produce a substantially homogeneous mixture. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve, the binder, and the matrix material, are in the same or different liquid, and are combined in any order, together, simultaneously, sequentially, or a combination thereof. In the preferred embodiment, the same liquid, preferably water is used. The molecular sieve, matrix material, and the binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, the binder and the matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray dryer is used as the forming unit, typically, the slurry of the molecular sieve, the binder and the matrix material is co-fed to the spray drying volume with a drying gas with an average inlet temperature ranging from 100° C. to 550° C., and a combined outlet temperature ranging from 50° C. to about 225° C. In an embodiment, the average diameter of the spray dried formed catalyst composition is from about 10 µm to about 300 µm, preferably from about 15 µm to about 250 µm, more preferably from about 18 µm to about 200 µm, and most preferably from about 20 µm to about 120 µm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve catalyst composition in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, preferably from about 10% to about 90%, more preferably from about 10% to about 80%, even more preferably from about 20% to about 70%, and most preferably from about 25% to about 60% by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 20 hours, preferably 1 hour to about 2 hours. In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particles size ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 15 weight percent per hour, preferably less than 10 weight percent per hour, more preferably less than 5 weight percent per hour, and even more preferably less than 2 weight percent per hour, and most preferably less than 1 weight percent per hour. In one embodiment, the molecular sieve catalyst composition or formulated molecular sieve catalyst composition has an ARI in the range of from 0.1 weight percent per hour to less than 5 weight percent per hour, more preferably from about 0.2 weight percent per hour to less than 3 weight percent per hour, and most preferably from about 0.2 weight percent per hour to less than 2 weight percent per hour.

V. Process for Using the Molecular Sieve Catalyst Compositions

The molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, New York 1977, which are all herein fully incorporated by reference. The preferred reactor type are riser reactors generally described in *Riser Reactor, Fluidization and Fluid-Particle Systems,* pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh liquid fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000 C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-}$, preferably from about 2 $hr^{-1}$ to about 3000 $hr^{-}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kpaa) to about 250 psia (1724 kpaa), more preferably from about 25 psia (172 kPaa) to about 150 psia (1034 kpaa), and most preferably from about 30 psia (207 kpaa) to about 60 psia (414 kpaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference. In yet another embodiment, a portion of the coked molecular sieve catalyst composition from the regenerator is returned directly to the one or more riser reactor(s), or indirectly, by pre-contacting with the feedstock, or contacting with a fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds,* Grace, Avidan and Knowlton, eds., Blackie, 1997 (336-337), which is herein incorporated by reference. Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology,* 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, $C_4$ and $C_5$ Olefinic Streams,* Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin.

In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

In another embodiment, the feedstock is fed to a reactor in an amount of greater than 16 Kg per hour, preferably greater than 32 Kg per hour, more preferably greater than 160 Kg per hour, even more preferably greater than 14,400 Kg per hour, and most preferably greater than 8,000,000 Kg per hour.

In one embodiment, the feedstock, preferably a feedstock comprising an oxygenate, more preferably a feedstock comprising methanol is fed to a reactor, preferably a reactor containing molecular sieve catalyst, as the conductivity level is monitored. The conductivity level is monitored to be within the desired conductivity limits so as not to adversely impact the molecular sieve catalyst. In particular, the conductivity level should either enhance selectivity of feedstock conversion to ethylene and propylene or have no significant effect on the selectivity. In addition, the conductivity level should not be so high as to significantly affect catalyst life.

In this invention, the feedstock can also be monitored for concentration of Group IA or IIA metals. The concentration levels of these metals correlate well with the desired conductivity levels, and more accurately reflect contamination levels in general. In one embodiment, the feedstock comprises methanol and/or dimethyl ether, and further comprises less than 50 wppm, preferably less than 40 wppm, more preferably less than 30 wppm, even more preferably less than 20 wppm, yet even more preferably less than 10 wppm, and most preferably less than 1 wppm of a Group IA metal salt and/or a Group IIA metal salt, preferably a Group IA metal salt such as sodium chloride and/or potassium chloride, based on total weight of the feedstock.

In another embodiment, the feedstock comprises at least 25 wppb of a Group IA metal salt and/or a Group IIA metal salt. More preferably the feedstock comprises at least 50 wppb, even more preferably at least 100 wppb, yet even more preferably at least 150 wppb, still even more preferably at least 250 wppb, and most preferably at least 500 wppb of a Group IA metal salt and/or a Group IIA metal salt, based on total weight of the feedstock.

In still another embodiment, the feedstock, preferably a feedstock comprising an oxygenate, more preferably a feedstock comprising methanol and/or dimethyl ether, further comprises in the range of from 10 wppb to about 50 wppm, preferably in the range of from about 10 wppb to about 40 wppm, more preferably in the range of from 15 wppb to about 30 wppm, even more preferably in the range of from 15 wppb to about 20 wppm, yet even more preferably in the range of from 10 wppb to about 10 wppm of a Group IA metal salt and/or a Group IIA metal salt, preferably a Group IA metal salt such as sodium chloride and/or potassium chloride, based on total weight of the feedstock.

In another embodiment, a feedstock is provided which has a substantially high concentration of a Group IA and/or Group IIA metal salt. An amount of the metal salt is removed from the feedstock to form a treated feedstock. The treated feedstock is provided to a reactor and contacted with molecular sieve to form an olefin product. In a particular embodiment, the amount of a Group IA and/or Group IIA metal salt in the feedstock is less than 10,000 wppm of a Group IA and/or Group IIA metal salt such as sodium chloride and/or potassium chloride, more preferably less than 5,000 wppm, even more preferably less than 1000 wppm, yet even more preferably less than 500 wppm, still even more preferably less than 250 wppm, and most preferably less than 100 wppm, based on total weight of the feedstock. This feedstock is then treated to reduce conductivity and contacted with molecular sieve to form olefin product.

In another embodiment, the feedstock which contains a substantially high concentration of a Group IA and/or Group IIA metal salt has a conductivity of not greater than about 750 uS/cm. Preferably, the feedstock which contains a substantially high concentration of a Group IA and/or Group IIA metal salt has a conductivity of not greater than about 500 uS/cm, more preferably not greater than about 300 uS/cm. The conductivity of the feedstock which contains the substantially high concentration of a Group IA and/or Group IIA metal salt is then reduced to more the more desirable conductivity levels prior to contact with molecular sieve catalyst.

In another embodiment, the feedstock, preferably an oxygenate, more preferably methanol and/or dimethylether is substantially free of a Group IA metal salt and/or a Group IIA metal salt, preferably a Group IA metal salt, and most preferably sodium chloride and/or potassium chloride. For the purposes of this patent specification and appended claims the term "substantially free" means that the feedstock comprises less than 30 ppm, preferably less than 29.4 ppm of a Group IA metal salt and/or a Group IIA metal salt, most preferably sodium chloride and potassium chloride or ions thereof.

Conventional well known chemical analysis techniques, such as Atomic Adsorption Spectroscopy (AAS), can be used to measure the amount of salts in the methanol feedstock. *Introduction to Zeolite Science and Practice*, H. van Bekkum, E. M. Flanigan, J. C. Janssen (editors), Elsevier, 1991, p. 259.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a. syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

VI. EXAMPLES

In order to provide a better understanding of the present invention including representative advantages thereof, the following examples are offered.

Example 1

By physical mixing sodium chloride (NaCl) or potassium chloride (KCl) with a SAPO-34 molecular sieve synthesized in accordance with well known procedures, (many of these procedures are discussed in this patent specification and are herein fully incorporated by reference) the SAPO-34 molecular sieve having a salt loading of 7.5 wt % was obtained. After mixing the salts and the molecular sieve, the combination was calcined for 5 hrs in $N_2$ followed by three hours in air at 650° C. An examination of the structural integrity of these mixtures was measured using well known X-ray diffraction techniques. In examining the XRD patterns of the untreated SAPO-34 molecular sieve versus the salt treated sieves, a clear reduction in XRD crystallinity was seen with the salt treated molecular sieves. In addition, the XRD pattern of the salt treated sieves showed a new peak, which is indicative of the formation of a new, unknown phase.

Examples 2 through 9

In these Examples 2 though 9, the same SAPO-34 molecular sieve used in Example 1 were mixed, separately, with salt solutions in methanol of the following salts: NaCl, $MgCl_2$ or $KNO_3$. The salt loadings on the molecular sieve ranged from about 80 to about 10,000 weight ppm. After mixing, the methanol was evaporated at temperatures between about 90° C. and about 120° C., and the formed dry solid was subsequently calcined for 5 hrs in $N_2$ followed by 3 hours in air at 650° C. The performance of these molecular sieve/salt mixtures were evaluated in a fixed bed reactor at 450° C., 25 WHSV and 25 psig (172 kpag). The reaction product was analyzed by on-line GC. Weight average light olefin selectivity (ethylene and propylene) were determined as well as catalyst life (measured in terms of grams of methanol converted per grams of molecular sieve). The results are summarized in Table 1 below.

TABLE 1

| Example | Salt type | Concentration (wppm on sieve) | -Cat. Life (gm MeOH converted per gm of sieve) | Selectivity (wt % ethylene + propylene) |
|---|---|---|---|---|
| Standard | None | 0 | 18.8 | 74.6 |
| 2 | NaCl | 84.0 | 16.7 | 75.0 |
| 3 | NaCl | 400.0 | 17.1 | 74.3 |
| 4 | NaCl | 4000.0 | 15.9 | 73.5 |
| 5 | NaCl | 10000.0 | 11.9 | 72.0 |
| 6 | $NaNO_3$ | 84.0 | 17.4 | 74.6 |
| 7 | $NaNO_3$ | 8400.0 | 16.1 | 72.4 |
| 8 | $MgCl_2$ | 84.0 | 18.1 | 74.1 |
| 9 | $MgCl_2$ | 8400.0 | 16.3 | 74.0 |

From Table 1 the negative effect of salt on catalyst life and light olefin selectivity is clearly demonstrated.

Example 10

This example illustrates the conversion of a Group IA and/or IIA metal salt based on total molecular sieve content to a Group IA and/or IIA metal salt in the oxygenate feedstock, for example in the methanol feed. Table 2 shows examples of NaCl concentrations in a methanol feed. These concentrations correspond to the respective NaCl concentrations on molecular sieve as shown above in Table 1. For the purposes of this example, the expected catalyst lifetime in a large scale MTO plant is six (6) months, and that a methanol feed pre-treatment step, for example, the vaporization system of the MTO plant, is capable of removing 99.9 wt % of the NaCl in the methanol feed before the vaporized methanol contacts the molecular sieve catalyst composition. The weight hourly space velocity of the methanol feed is 25 $hr^{-1}$. It is also understood that a lower percentage removal less than 99.9 wt % would result in lower amount of a Group IA and/or IIA metal salt present in the feed or in contact with the catalyst.

TABLE 2

| NaCl Concentration (weight ppm on molecular sieve) | NaCl concentration in methanol feed (weight ppm) |
|---|---|
| 0.0 | 0.0 |
| 84.0 | 0.6 |
| 400 | 2.9 |
| 4000 | 29.4 |
| 10000 | 73.1 |

Example 11

Seawater from off the coast of Stavienisse, a village located on the western point of the island of Tholen, the Netherlands, was collected at −21 meters. A sample of the seawater was mixed with pure methanol (Merck, p.a.), and conductivity was measured using a Schott Geräte Conductivity meter (Tyoe CG857), equipped with a LF100 conductivity probe. Samples of the mixed methanol and seawater were further diluted with methanol at various concentrations, and the conductivity measured. The results are shown in Table 3.

TABLE 3

| Sample # | MeOH (gm.) | Seawater (gm.) | Sample 1 (gm.) | Sample 3 (gm.) | Conc. (wppm) | Ave. Cond. (uS/cm) |
|---|---|---|---|---|---|---|
| 1 | 34.6164 | 0.04146 | | | 1196 | 46.4 |
| 2 | 23.27021 | | 8.0215 | | 307 | 12.8 |
| 3 | 88.85 | | 9.8400 | | 119 | 7.8 |
| 4 | 22.027 | | | 5.6109 | 30 | 3.9 |
| 5 | 28.6091 | | | 2.5944 | 11 | 3.4 |

Example 12

Additional seawater samples from the seawater described in Example 11 were diluted with methanol and the conductivity of the mixtures were measured. The results are shown in Table 4.

TABLE 4

| Sample # | MeOH (gm.) | Seawater (gm.) | Conc. (wppm) | Cond. (1) (uS/cm) | Cond. (2) (uS/cm) | Ave. Cond. (uS/cm) |
|---|---|---|---|---|---|---|
| 1 | 15.000 | 0.000 | 0 | 0.7 | 0.7 | 0.7 |
| 1 | 14.99 | 0 | 0 | 1.5 | 1.2 | 1.35 |
| 2 | 16.74942 | 0.00647 | 386 | 18.5 | 18.5 | 18.5 |
| 3 | 15.04122 | 0.02028 | 1346 | 54.8 | 54.5 | 54.65 |
| 4 | 14.64419 | 0.02196 | 1497 | 56.8 | 56.7 | 56.75 |
| 5 | 15.23638 | 0.02866 | 1877 | 66.3 | 66 | 66.15 |
| 6 | 15.45856 | 0.04632 | 2987 | 102.9 | 102.7 | 102.8 |
| 2 | 13.330 | 0.063 | 4700 | 147.9 | 147.5 | 147.7 |
| 3 | 15.511 | 0.121 | 7800 | 235 | 238 | 236.5 |
| 4 | 15.535 | 0.190 | 12,200 | 342 | 341 | 341.5 |
| 5 | 15.452 | 0.250 | 16,200 | 439 | 443 | 441 |
| 6 | 15.103 | 0.317 | 21,000 | 542 | 534 | 538 |

While the present invention has been described and illustrated by reference to particular embodiments, those of ordinary skill in the art will appreciate that the invention lends itself to variations not necessarily illustrated herein. For example, it is contemplated that there are many ways of removing a salt from a feedstock comprising an oxygenate such as by boiling (i.e., distillation), methanol vapor/water absorbant absorber, and even ion exchange via a resin bed reactor using a sulfonated polystyrene resin. For this reason, then, reference should be made solely to the appended claims for purposes of determining the true scope of the present invention.

The invention claimed is:

1. A process for converting a feedstock comprising an oxygenate, the process comprising the steps of:
    (a) introducing the feedstock to a reactor system in the presence of a molecular sieve catalyst composition comprising a molecular sieve, wherein the amount of a Group IA metal salt and/or Group IIA metal salt based on the molecular sieve is less than 10,000 ppm;
    (b) withdrawing from the reactor system an effluent stream;
    (c) passing the effluent stream through a recovery system; and
    (d) recovering at least one or more olefin(s) in amount greater than 1,000 Kg/day.

2. The process of claim 1 wherein the effluent steam is Original at a rate greater than 1,000 Kg/hour.

3. The process of claim 1 wherein the feedstock is introduced to the reactor at a rate greater than 1,000 Kg/hour.

4. The process of claim 1 wherein the process is producing greater than 10,000 Kg per day of the one or more olefin(s).

5. The process of claim 1 wherein the amount of a Group IA metal salt and/or Group IIA metal salt based on the molecular sieve is less than 5000 ppm.

6. The process of claim 1 wherein the amount of a Group IA metal salt and/or Group IIA metal salt based on the molecular sieve is less than 1000 ppm.

7. The process of claim 1 wherein the amount of a Group IA metal salt and/or Group IIA metal salt based on the molecular sieve is less than 500 ppm.

8. The process of claim 1 wherein the amount of a Group IA metal salt and/or Group IIA metal salt based on the molecular sieve is less than 250 ppm.

9. The process of claim 1 wherein the amount of a Group IA metal salt and/or Group IIA metal salt based on the molecular sieve is less than 100 ppm.

10. The process of claim 1 wherein the oxygenate comprises methanol and less than 50 ppm of a Group IA and/or Group IIA metal salt.

11. A process for converting oxygenate to olefin, comprising the steps of:
    a) providing an oxygenate composition having a positive conductivity of not greater than 10 uS/cm. and containing at least one Group IA or Group IIA metal salt; and
    b) contacting the oxygenate composition with a molecular sieve to convert oxygenate in the oxygenate composition to olefin.

12. The process of claim 11, wherein the conductivity of the provided oxygenate composition is at least 1.5 uS/cm.

13. The process of claim 11, wherein the conductivity of the provided oxygenate composition is not greater than 5 uS/cm.

14. The process of claim 11, wherein the oxygenate composition contains at least one lithium, sodium, or potassium salt.

15. The process of claim 14, wherein the oxygenate composition contains at least one halide salt of lithium, sodium, or potassium.

16. The process of claim 15, wherein the oxygenate composition contains at least one chloride salt of lithium, sodium, or potassium.

17. The process of claim 11, wherein the oxygenate composition contains at least one magnesium or calcium salt.

18. The process of claim 17, wherein the oxygenate composition contains at least one halide salt of magnesium or calcium.

19. The process of claim 11, wherein the oxygenate composition contains sodium chloride.

20. The process of claim 11, wherein the provided oxygenate composition contains at least one Group IA or Group IIA metal salt in the range of from 10 wppb to 50 wppm, based on total weight of the oxygenate composition.

21. The process of claim 20, wherein the provided oxygenate composition contains at least one Group IA or Group IIA metal salt in the range of from 15 wppb to 30 wppm, based on total weight of the oxygenate composition.

22. The process of claim 11, further comprising the step of converting the olefin to polyolefin.

23. A process for converting oxygenate to olefin, comprising the steps of:
   a) providing an oxygenate composition containing at least one Group IA or Group IIA metal salt;
   b) reducing conductivity of the oxygenate composition to form a treated feedstock having a conductivity of not greater than 10 uS/cm; and
   c) contacting the treated feedstock with a molecular sieve to convert oxygenate in the oxygenate composition to olefin.

24. The process of claim 23, wherein the provided oxygenate composition has a conductivity of not greater than 750 uS/cm.

25. The process of claim 24, wherein the provided oxygenate composition has a conductivity of not greater than 500 uS/cm.

26. The process of claim 25, wherein the provided oxygenate composition has a conductivity of not greater than 300 uS/cm.

27. The process of claim 23, wherein the treated feedstock has a positive conductivity.

28. The process of claim 27, wherein the conductivity of the treated feedstock is at least 1.5 uS/cm.

29. The process of claim 23, wherein the conductivity of the treated feedstock is not greater than 5 uS/cm.

30. The process of claim 23, wherein the treated feedstock contains at least one lithium, sodium, or potassium salt.

31. The process of claim 30, wherein the treated feedstock contains at least one halide salt of lithium, sodium, or potassium.

32. The process of claim 31, wherein the treated feedstock contains at least one chloride salt of lithium, sodium, or potassium.

33. The process of claim 23, wherein the treated feedstock contains at least one magnesium or calcium salt.

34. The process of claim 33, wherein the treated feedstock contains at least one halide salt of magnesium or calcium.

35. The process of claim 23, wherein the treated feedstock contains sodium chloride.

36. The process of claim 23, wherein the treated feedstock contains at least one Group IA or Group IIA metal salt in the range of from 10 wppb to 50 wppm, based on total weight of the oxygenate composition.

37. The process of claim 36, wherein the treated feedstock contains at least one Group IA or Group IIA metal salt in the range of from 15 wppb to 30 wppm, based on total weight of the oxygenate composition.

38. The process of claim 23, Further comprising to step of converting the olefin to polyolefin.

* * * * *